United States Patent [19]

Gaiser

[11] 4,327,056
[45] Apr. 27, 1982

[54] DEODORANT DISPENSER

[76] Inventor: Conrad J. Gaiser, P.O. Box 534, Zephyr Cove, Nev. 89448

[21] Appl. No.: 195,599

[22] Filed: Oct. 9, 1980

[51] Int. Cl.$^3$ .............................................. A61L 9/12
[52] U.S. Cl. .................................... 422/124; 239/44; 239/51.5; 239/55; 239/56; 239/57; 239/59; 239/60; 422/4; 422/123
[58] Field of Search ...................... 422/4, 5, 122, 123, 422/124, 306; 239/44, 51.5, 55, 56, 57, 59, 60

[56] References Cited

U.S. PATENT DOCUMENTS

| 525,497 | 9/1894 | Hoffman | 43/129 |
|---|---|---|---|
| 1,614,817 | 1/1927 | Andrew | 422/124 |
| 2,585,339 | 2/1952 | Miller | 422/124 |
| 2,997,282 | 8/1961 | Binter et al. | 239/57 X |
| 4,146,566 | 3/1979 | Gaiser | 422/122 |
| 4,258,004 | 3/1981 | Valenzona et al. | 239/57 X |

FOREIGN PATENT DOCUMENTS 770896  9/1934  France ................ 422/306

Primary Examiner—Barry Richman
Attorney, Agent, or Firm—Fischer, Tachner & Strauss

[57] ABSTRACT

A deodorant dispensing package having two rates of discharge of deodorant. The package is provided with air circulation ports for a low, continuous release of deodorant and a manual pump for a high, forced rate of deodorant discharge for sudden odors. The package is formed of two telescoping housing members with an internal wall portion that divides the housing into inner and outer compartments. The housing contains a deodorant reservoir and the inner and outer compartments are each provided with vent ports communicating externally of the housing. The inner and outer compartments also communicate through an interior port in the internal wall and a deodorant discharge surface is located in the inner compartment between the inner port and the inner compartment external vent port. Air circulation through the vent ports is sufficient to provide the low rate of air freshener activity. The manual contraction and expansion of the telescoping housing members provides a high rate of deodorant discharge. Preferably a bellows is provided in the outer compartment to facilitate the pumping action. Also preferably, the vent port from the inner compartment is provided with variable aperture means whereby its degree of opening can be fixedly adjustable. The package is intended for use with replaceable canisters of deodorant which can be in liquid form, impregnated or incorporated in a gel solid, or absorbed in a sponge or other carrier.

12 Claims, 4 Drawing Figures

DEODORANT DISPENSER

BACKGROUND OF THE INVENTION

There has occurred recently a demand for the dual action household deodorant dispenser. These dispensers provide a continuous discharge of deodorant, and have some facility for an accelerated discharge of deodorant. In my prior U.S. Pat. No. 4,146,566, I disclose a deodorant dispenser which has a collapsible wall portion and internal valving to provide a pump permitting the user to forcefully pump air through a bed of solids on which the deodorant is abosrbed. The flow resistance of a solid bed of absorbent complicates the structure of this dispenser some what, requiring the use of internal check valves and the like to provide a positive pumping action.

BRIEF DESCRIPTION OF THE INVENTION

This invention comprises a simple deodorant dispenser having a dual action; a low rate of deodorant discharge for air freshening and a high rate of forced deodorant discharge for sudden odors. The package is formed with a housing of two housing members which are telescopically assembled. Preferably the members are resiliently biased into their expanded telescoping positions. An internal wall is provided to divide the housing into inner and outer compartments, each of which is provided with external port means. Internal port means provide communication between the compartments. A deodorant vaporization surface is located in the inner compartment, between the internal port means and the external vent port means. Preferably, the external vent port means is provided with variable aperture means to provide a fixed adjustability in the degree of opening of the vent port means and, also preferably, the outer compartment is provided with a bellows. Air circulation through the device is sufficient to provide the slow rate of deodorant discharge desired for air freshening. The repeated, manual compressing and expanding of the assembly of housing members provides a pumping action to achieve a forced circulation of air through the package at a rate sufficient to provide a high rate of deodorant discharge. Preferably, the package is provided with a removeable or replaceable canister containing a reservoir of deodorant.

BRIEF DESCRIPTION OF THE DRAWINGS

The invention will be described with reference to the FIGS. of which.

DESCRIPTION OF PREFERRED EMBODIMENTS

Figures 1, 2, 3, 4:
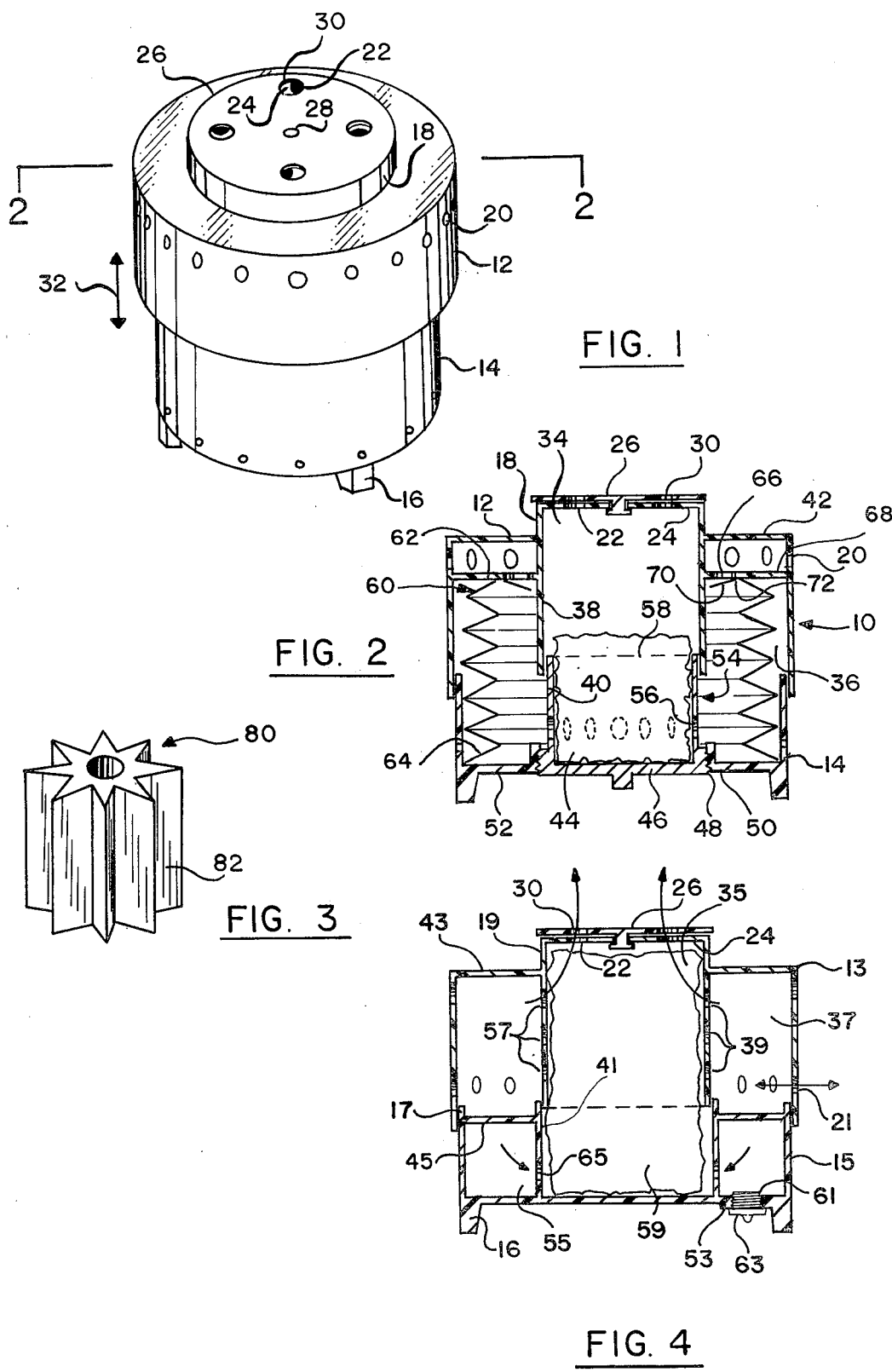
FIG. 1 is a perspective view of the dispenser package of the invention.
FIG. 2 is a view along lines 2—2 of FIG. 1.
FIG. 3 is an illustration of a solid gel deodorant useful in the embodiments of FIGS. 1 and 2.
FIG. 4 is a cross-sectional elevational view of another embodiment of the dispenser of the invention.

Referring now to FIG. 1, the invention is illustrated as a dispensing package 10 formed by first and telescoping housing members 12 and 14, respectively. The lower member 14 can be provided with legs 16 and the upper member 12 can carry a centrally located cylindrical boss 18. The first series of external vents 20 are provided about the periphery of the upper housing member 12 and a second series of vent ports 22 can be provided in the end surface 24 of the boss 18. Preferably, at least one of these series of vent ports is provided with a variable closure such as disc 26 which is pivotally mounted on pin 28 and which has a plurality of apertures 30 that can be rotated into and out of alignment with the vent ports 22, thereby providing a fixed adjustability in the degree of opening of the vent ports 22. The first and second housing members 12 and 14 are mounted in a telescoping assembly, permitting their relative axial extension and contraction as indicated by the double arrowhead line 32.

Referring now to FIG. 2, the invention will be described in greater detail. As shown in FIG. 2, the package 10 is subdivided into inner and outer compartments 34 and 36 by internal wall means such as the cylindrical inner wall 38 carried by the upper housing member 12 and the co-acting, received cylindrical wall 40 which is centrally secured to the lower housing member 14. The inner cylindrical wall 38 projects above the end plate 42 of the upper housing member 12 to provide the cylindrical boss 18 previously described with the end wall 24 having the vent ports 22 and the disc closure member 26 with its plurality of apertures 30 that can be rotated into and out of alignment with the vent ports 22.

The housing contains a reservoir of deodorant which, preferably, is removably secured in the assembly in a canister 44. The canister 44 is formed with an end plug 46 having external threads 48 which can be threadably received in a internally threaded aperture 50 in the bottom wall 52 of the lower housing member 14. The plug 46 has a cylindrical sleeve 54 dependent therefrom which provides the inner cylindrical wall 40 previously referred to that is telescopically received within the cylindrical inner wall 38. A plurality of apertures 56 are provided in the lower portion of wall 40 of sleeve 54 thereby providing internal port means communicating between inner compartment 34 and outer compartment 36 of the housing.

The deodorant reservoir in the package can comprise a solid form deodorant generally designated at 58. This can be a porous, open celled solid carrier such as a sponge and the like which contains, within its pores, the deodorant composition.

The outer compartment 36 can be provided with a bellows 60 to assist the forced air circulation through the package and to provide a resilient biasing of the first and second housing numbers into their extended position. Alternatively, a helical coil spring could be provided in this compartment to resiliently bias these members into their illustrated extended positions. When the bellows 60 are provided, the upper edge 62 of the bellows is cemented to the upper housing member 12 and the lower edge 64 thereof is cemented to the lower housing 14, thereby providing a pump to force air through the assembly. The first series of external vent ports 20 are in the upper end of the upper housing member 12 and these communicate internally of bellows 60 through apertures 66 which are located in the internal end wall 68 of the upper housing member 12. If desired, a simple flapper check type valve 70 can be positioned adjacent the apertures 66. This can simply be an annular ring which is bonded about one edge such as 72 to the under surface of the internal end wall 68.

The operation of the deodorant package thus described is relatively apparent from its construction. The package provides adequate venting of the deodorant reservoir to the atmosphere for normal air freshening action, the air flowing into the canister through external vent ports 20 and 22 and passing over the reservoir and the deodorant exchange surface such as sponge 58, and exiting through external vent ports 20 or 22. When an accelerated rate of discharge of deodorant is desired, the user simply compresses the assembly, generating a pump action which forces air from the bellows 60 through the internal vents 56, across the deodorant vaporization surface such as sponge 58 and into the atmosphere through the vent ports 22 of the inner compartment. When the reservoir of deodorant is substantially depleted, the removeable plug 46 can be removed from the package and a new supply such as a sponge 58 which is saturated with the deodorant can be replaced for the expanded sponge.

Referring now to FIG. 3, there is illustrated an alternative form of the deodorant that is useful in the package in FIG. 2. As illustrated in FIG. 3, the deodorant is contained in a solid gel body 80 which can be of various geometrical shapes to provide an extended surface. Various suitable shapes can be used; a suitable shape is that illustrated having a generally star form cross section configuration shown in FIG. 3 to provide the expanded vaporization surface 82.

Referring now to FIG. 4, there is illustrated a crossectional elevational view of an alternative construction. In this embodiment, upper and lower housing members 13 and 15 are telescopically assembled and the upper housing member 13 bears an internal wall such as the centrally located cylindrical sleeve 39. The latter is provided with a plurality of apertures 57 to provide communication between the inner compartment 35 and outer compartment 37. The upper end of the cylindrical wall 39 can extend past the end wall 43 of the upper member thereby providing a raised boss 19 on this member. The raised boss has an end plate 24 with external vent ports 22 such as previously described. This end wall 24 also supports a closure disc 26 that is pivotally mounted thereon and that has a plurality of apertures 30 that can be rotated into and out of alignment with the vent ports 22, thereby providing a fixed adjustability in the open area of the ports, all as described with reference to these same elements in FIGS. 1 and 2.

The lower housing member 15 can be provided with lower support legs 16. The lower member has an annular internal compartment formed by the upper end wall 45 and the internal centrally located cylindrical wall 41. The latter telescopically receives the internal cylindrical wall 39 of the upper housing member 12. The inner compartment 35 which is thereby formed, is filled substantially entirely by an open pore, porous and elastic body 59, e.g., a cellulosic sponge. The annular chamber 55 of the lower housing member 15 provides a reservoir for the deodorant which can be loaded therein in liquid form through the aperture 61 in the bottom wall 53 of the lower housing member 15. The aperture 61 can be threaded to receive a threaded closure plug 63.

A plurality of apertures 65 are provided in the lower portion of the cylindrical wall 41 to permit the liquid deodorant within the lower compartment 55 to maintain the sponge 59 in a saturated condition.

The plurality of apertures 21 are preferably provided in the lower portion of the cylindrical outer wall of the upper housing member.

The operation of the dispensing package of FIG. 4 is substantially similar to that of FIGS. 1 and 2. The package provides for a slow release of deodorant for air freshening; air circulation being provided through external vent ports 21 and 22 and through the internal apertures 57, insuring air flow across the extended evaporation surface provided by the sponge 59. When an accelerated discharge of deodorant is desired, the user compresses the assembly. As the assembly is telescopically compressed, the external vent ports 21 are closed by the upper end 17 of the lower housing member 15. This serves to force the air trapped in the outer compartment through apertures 57, sponge 59 and into the atmosphere through apertures 22. When the user releases the assembly, the resiliency of the sponge 59 will be sufficient to extend the assembly for repeated compression. In this operation the sponge 59 serves as an evaporation surface as well as a resilient means providing a force to restore the assembly into its extended position illustrated in FIG. 4. If desired, a helical coil spring can be located in the outer compartment 37 to assist the extension of the assembly into the extended period.

The assembly can be readily recharged with fresh supplies of liquid deodorant simply by inverting the assembly, removing plug 63 and pouring the liquid into the annular reservoir 55. Plug 63 is then inserted to close the compartment and the package is ready for reuse. During the use of the deodorant package, the liquid deodorant will pass through apertures 65 into contact with the sponge 59 maintaining this sponge saturated with the deodorant throughout its use.

The invention as thus described provides for a very simple yet highly functional deodorant dispensing package. The package is provided with a minimum number of moving parts yet it provides for a slow release of deodorant for air refershing purposes and permits an accelerated dispensing of deodorant when desired.

The invention has been described with reference to the illustrated and preferred embodiments. It is not intended that it be unduly limited by this disclosure of the presently preferred embodiments. Instead, it is intended that the invention be defined by the various means and their equivalents, set forth in the following claims.

What is claimed is:
1. A deodorant dispensing package for static and forced dispensing of a deodorant which comprises:
   (a) first and second telescoping movable housing members defining a closed chamber;
   (b) internal walls dependent therefrom defining inner and outer compartments within said closed chamber;
   (c) a deodorant composition within said closed chamber;
   (d) first port means in said housing members venting said inner compartment externally of said housing;
   (e) second port means in said housing communicating between said inner and outer compartments;
   (f) a deodorant vaporization surface wetted with said deodorant composition located within said inner compartment between said first and second port means;
   (g) third port means in said housing members venting said outer compartment externally of said housing;
   (h) resilient means biasing said first and second housing members into an expanded position; and
   (i) means limiting venting of said outer compartment through said third port means whereby the telescopic movement of said members forces air from said package.

2. The deodorant dispensing package of claim 1 wherein said deodorant composition comprises a replaceable cartridge removeably secured to one of said first and second housing members.

3. The deodorant dispensing package of claim 1 wherein said resilient means is a bellows contained in said outer compartment.

4. The deodorant dispensing package of claim 1 including closure means for the fixed adjustability of the flow area of said first port means.

5. The deodorant dispensing package of claim 1 wherein said resilient means is an open-celled, porous, elastic body which also serves as said deodorant vaporization surface.

6. The deodorant dispensing package of claim 1 wherein said deodorant vaporization surface is the surface of a solid form carrier inpregnated with the deodorant composition.

7. A deodorant dispensing package of claim 1 wherein said means limiting venting is a flapper valve member secured in said outer compartment adjacent to said third port means and operative to close said third port means upon contraction of said members.

8. The deodorant dispensing package of claim 1 wherein said first and second housing members are cylindrical.

9. The deodorant dispensing package of claim 8 wherein the upper one of said cylindrical housing members carries a central cylindrical wall which telescopically receives a central, cylindrical deodorant cartridge carried by the lower of said housing members.

10. The deodorant dispensing package of claim 9 including an apertured cover plate on the outside end of said cylindrical wall to enclose said inner compartment and to provide said first port means.

11. The deodorant dispensing package of claim 9 wherein said deodorant cartridge is removeably secured to the lower of said housing members.

12. The deodorant dispensing package of claim 11 wherein said deodorant is contained in a cylindrical canister which is telescopically received in said cylindrical wall.

* * * * *